(12) United States Patent
Bedingfield et al.

(10) Patent No.: US 6,746,514 B2
(45) Date of Patent: Jun. 8, 2004

(54) GAS VENTING DEVICE AND A SYSTEM AND METHOD FOR VENTING A GAS FROM A LIQUID DELIVERY SYSTEM

(75) Inventors: John Bedingfield, Largo, FL (US); Li Pan, Tampa, FL (US); John A. Parish, Clearwater, FL (US)

(73) Assignee: Baxter International Inc., Deerfield, IL (US)

( * ) Notice: Subject to any disclaimer, the term of this patent is extended or adjusted under 35 U.S.C. 154(b) by 28 days.

(21) Appl. No.: 10/216,476

(22) Filed: Aug. 8, 2002

(65) Prior Publication Data

US 2004/0025693 A1 Feb. 12, 2004

(51) Int. Cl.⁷ .............................................. B01D 19/00
(52) U.S. Cl. ...................................... 95/46; 96/6; 96/10
(58) Field of Search ......................... 95/46, 241; 96/6, 96/10, 155, 187

(56) References Cited

U.S. PATENT DOCUMENTS

| | | | |
|---|---|---|---|
| 3,631,654 A | * | 1/1972 | Riely et al. ....................... 96/6 |
| 3,915,646 A | | 10/1975 | Harris et al. |
| 4,345,999 A | * | 8/1982 | Sigdell et al. ..................... 96/6 |
| 4,461,165 A | * | 7/1984 | Kesson ....................... 73/19.05 |
| 4,484,936 A | * | 11/1984 | Sakai .......................... 96/219 |
| 4,516,580 A | * | 5/1985 | Polanyi ....................... 600/364 |
| 4,618,343 A | | 10/1986 | Polaschegg |
| 4,788,556 A | * | 11/1988 | Hoisington et al. ........... 347/92 |
| 4,986,837 A | * | 1/1991 | Shibata ............................. 96/6 |
| 5,045,096 A | * | 9/1991 | Quang et al. .................. 96/155 |
| 5,306,472 A | * | 4/1994 | Sano et al. ................. 422/211 |
| 5,312,295 A | | 5/1994 | Young |
| 5,779,674 A | | 7/1998 | Ford |
| 5,944,684 A | | 8/1999 | Roberts et al. |
| 5,980,481 A | | 11/1999 | Gorsuch |
| 6,234,991 B1 | | 5/2001 | Gorsuch |
| 6,254,567 B1 | | 7/2001 | Treu et al. |
| 6,274,103 B1 | | 8/2001 | Taylor |
| 6,309,444 B1 | * | 10/2001 | Sims et al. ..................... 95/46 |
| 6,315,815 B1 | * | 11/2001 | Spadaccini et al. ............ 95/46 |
| 6,347,711 B1 | | 2/2002 | Goebel et al. |
| 6,402,810 B1 | * | 6/2002 | Mayer et al. .................. 95/46 |
| 6,409,699 B1 | | 6/2002 | Ash |
| 6,426,056 B2 | | 7/2002 | Taylor |
| 2001/0027289 A1 | | 10/2001 | Treu et al. |
| 2002/0112609 A1 | | 8/2002 | Wong |
| 2002/0123715 A1 | | 9/2002 | Sorenson et al. |
| 2003/0173278 A1 | * | 9/2003 | Inoue et al. ................. 210/188 |

FOREIGN PATENT DOCUMENTS

| | | |
|---|---|---|
| DE | 19928476 A1 | 6/1999 |
| EP | 1051955A2 A3 | 4/2002 |

\* cited by examiner

Primary Examiner—Robert H. Spitzer
(74) Attorney, Agent, or Firm—Paula J. F. Kelly; Joseph P. Reagen; Bell, Boyd & Lloyd LLC (57) ABSTRACT

An apparatus, a system and a method for venting a gas from a liquid delivery system are provided. A venting tube may be provided and may be positioned within a chamber that contains the liquid. The liquid may have a top surface within the chamber. The venting tube may have an opening covered by a liquiphobic membrane or a hydrophobic membrane. The membrane may define a plane or a surface which is not parallel to the top surface of the liquid. Gas may pass through a portion of the membrane into the venting tube. Moreover, the membrane may vent the gas. The membrane is non-parallel to the liquid, and, as a result, the membrane may be less prone to clogging.

31 Claims, 6 Drawing Sheets

GAS VENTING DEVICE AND A SYSTEM AND METHOD FOR VENTING A GAS FROM A LIQUID DELIVERY SYSTEM

BACKGROUND OF THE INVENTION

The present invention relates to an apparatus, a system and method for venting a gas from a liquid delivery system. More specifically, the apparatus relates to a venting tube which may be implemented within a liquid delivery system. The venting tube has a liquiphobic membrane through which the gas may escape from the liquid delivery system through the venting tube without clogging of the membrane.

It is generally known to introduce liquids into the body, including medicaments and supplements, as well as bodily liquids, such as blood, plasma or the like. Often, a liquid delivery system is used to introduce these materials. The liquid delivery system may include a tube or other container which houses the liquid while the liquid is introduced into the body. Often, gas bubbles may form within the liquid. If the gas is introduced into the human body, the gas can be potentially harmful.

In some applications, hydrophobic membranes are incorporated into the liquid delivery system to vent the gas from the liquid delivery system. The membrane may be attached to a venting tube at an opening of the venting tube. The venting tube may be positioned along a path of the liquid prior to the liquid entering the body. The membrane may be gas permeable and may have pores through which gas may pass through the membrane into the venting tube. The gas may be present within the liquid or may be present within a chamber holding the liquid. The gas which enters the venting tube may then be vented from the system. The hydrophobic nature of the membrane prevents liquid from passing through the membrane. Accordingly, when the liquid contacts the membrane, gas escapes from the liquid and passes through the membrane. The gas may then be vented from the system.

However, a number of deficiencies exist with known systems and methods for removing gas from liquid delivery systems. For instance, known membranes incorporated along a liquid delivery path in a direction parallel to the path of the liquid are prone to clogging. For example, a liquid delivery system may use a liquid having glucose and/or ionic components. As gas from the liquid passes through the membrane, the glucose and/or the ionic components may accompany the gas and may become trapped within the pores of the membrane. The glucose and/or the ionic components may eventually infiltrate the membrane and may prevent venting of the gas from the liquid, resulting in a loss of hydrophobicity. Because the membrane is positioned parallel to the path of the liquid in known systems, the entire surface of the membrane is exposed to the liquid and becomes clogged during venting.

In other applications, liquid pressure may be non-constant, as seen in applications using a pump, such as a piston pump, for liquid delivery. Increases in pressure may cause, for example, pressure spikes which may damage the membrane and/or shorten the time that the membrane may be used within the system.

In addition, certain applications incorporate a mechanical float valve vent to vent the gas from the liquid delivery system. Often, these vents still require the use of a membrane within the system to prevent liquid contamination. Having a mechanical float valve and membrane substantially increases the cost associated with venting gas from the liquid delivery system. A need, therefore, exists for an apparatus, a system and a method for venting a gas from a liquid delivery system wherein the gas is vented through a liquiphobic membrane that is not prone to damage from pressure spikes or clogging

SUMMARY OF THE INVENTION

The present invention relates to an apparatus, a system and a method for venting a gas from a liquid delivery system. More specifically, the present invention relates to an apparatus that includes a venting tube positioned within a chamber. The chamber may hold a volume of liquid wherein the liquid has a top surface. Gas may be trapped within the chamber above the top surface of the liquid. Gas bubbles may be formed within the liquid as a result of dissolved gas coming out of solution due to, for example, movement of the liquid, change in liquid temperature or pressure, addition of liquid, or the like. These gas bubbles may be trapped in the upper portion of the chamber.

The venting tube may have walls defining an interior and an opening located at a bottom end of the venting tube. The opening may be covered by a liquiphobic membrane having a surface for contacting the fluid within the chamber. The membrane may prevent the liquid from entering the venting tube and may allow the gas trapped within the chamber to escape through the membrane into the venting tube for venting from the liquid delivery system. The membrane may be positioned along the venting tube at an angle wherein the membrane is not parallel to the top surface of the liquid within the chamber. As a result, the membrane may be less prone to clogging. The venting tube may also vent the gas independent of a position of the liquid in the chamber as long as the membrane is exposed to the gas, and a positive pressure exists within the liquid delivery system relative to ambient pressure.

To this end, in an embodiment of the present invention, a method for venting a gas from a liquid delivery system is provided. The method comprises the steps of: holding a liquid having a surface within a chamber having an interior wherein a portion of the chamber extends into the interior wherein the portion which extends into the interior forms a non-parallel surface to the surface of the liquid and further has a hole; and attaching a liquiphobic membrane to the portion of the chamber which extends towards the interior wherein the membrane is within the interior of the chamber and further wherein the liquiphobic membrane covers the hole.

In an embodiment, the method comprises the step of adding liquid to the interior of the chamber.

In an embodiment, the method comprises the step of removing the gas from the chamber.

In an embodiment, the method comprises the step of venting the gas through the hole in the portion of the chamber which extends towards the interior of the chamber.

In an embodiment, the liquiphobic membrane conforms to the shape of the non-parallel surface.

In an embodiment, the non-parallel surface is non-planar.

In another embodiment of the present invention, a method for venting a gas from a liquid delivery system is provided. The method comprises the steps of: providing a tube having walls defining an interior wherein the tube has an opening; attaching a gas-permeable membrane to the tube wherein the membrane covers the opening; and placing the tube to extend within a chamber having walls defining an interior wherein the chamber holds the liquid having a top surface within the chamber and further wherein the membrane defines a surface that is not parallel to the top surface of the liquid.

In an embodiment, the method comprises the step of adding liquid in the interior of the chamber.

In an embodiment, the method comprises the step of venting gas through the tube wherein the gas exits the tube exterior to the interior of the chamber.

In an embodiment, the method comprises the step of venting gas through holes in the walls of the tube exterior to the interior of the tube.

In an embodiment, the method comprises the step of providing a second opening in the tube wherein the second opening is covered by the membrane.

In another embodiment of the present invention, an apparatus for venting a gas from a liquid delivery system is provided. The apparatus has a tube having an interior defined by walls having a length defined between a first end and a second end wherein the tube has a top surface at the first end wherein the top surface defines a plane. An opening is provided at the second end of the tube wherein the opening defines a plane wherein the plane of the opening is not parallel to the plane of the top surface. Also provided is a membrane covering the opening of the tube wherein the membrane prevents the liquid from passing into the interior of the tube and allows the gas to enter into the interior of the tube through the opening of the tube.

In an embodiment, a venting hole is provided in the walls of the tube.

In an embodiment, the plane defined by the opening is perpendicular to the plane defined by the top surface.

In an embodiment, the walls of the tube form an apex at the second end.

In an embodiment, a second opening is provided in the walls of the tube wherein the membrane covers the second opening.

In an embodiment, the membrane is attached to the venting tube at a point on the wall between the top surface and the opening.

In an embodiment, the walls of the tube at the second end are rounded.

In another embodiment of the present invention, a system for venting a gas from a liquid delivery system is provided. The system has a first tube having walls defining an interior wherein the first tube has a first opening. The system also has a chamber having walls defining an interior with an opening in one of the walls wherein the interior holds the liquid wherein the liquid has a top surface and further wherein the first tube extends into the interior of the chamber through the opening. Also provided is a membrane covering the first opening of the first tube wherein the membrane is gas-permeable and defines a surface that is not parallel to the top surface of the liquid.

In an embodiment, the system has a gas pocket within the interior of the chamber defined by a volume of the interior which does not contain the liquid.

In an embodiment, the system has a venting hole in the wall of the first tube wherein the venting hole is exterior to the walls of the chamber.

In an embodiment, a liquid input port is provided in one of the walls of the chamber.

In an embodiment, a liquid exit port is provided in one of the walls of the chamber.

In an embodiment, a second opening is provided in the walls of the first tube wherein the membrane covers the second opening.

In an embodiment, the walls of the first tube form an apex.

In an embodiment, the system has a second tube within the interior of the chamber wherein the second tube is flexible and attached to a weight.

In another embodiment of the present invention, an apparatus for venting a gas from a liquid delivery system is provided. The apparatus has a chamber having a body defining an interior holding a liquid wherein the chamber traps gas within the interior. A depression is integrally formed with the body wherein the depression has an inside surface within the interior of the chamber wherein the liquid within the interior of the chamber has a surface defining a plane. An input port is provided on the chamber wherein the input port allows entry of the liquid into the chamber. An exit port is also provided on the chamber wherein the liquid within the chamber exits the chamber through the exit port. A liquiphobic membrane is positioned on the inside surface of the depression wherein the liquiphobic membrane defines a surface which is non-parallel to the plane defined by the surface of the liquid within the chamber.

In an embodiment, the membrane is attached to the inside surface of the depression.

In an embodiment, a hole is provided in the depression wherein the membrane covers the hole.

In an embodiment, the input port is below the surface of the liquid.

In an embodiment, the exit port is below the surface of the liquid.

It is, therefore, an advantage of the present invention to provide an apparatus, a system and a method for venting a gas from a liquid delivery system which prevents clogging of a gas-permeable liquiphobic membrane used to vent the gas.

Another advantage of the present invention is to provide an apparatus, a system and a method for venting a gas from a liquid delivery system which vents gas from the liquid independent of a position of the membrane within the liquid delivery system.

Yet another advantage of the present invention is to provide an apparatus, a system and a method for venting a gas from a liquid delivery system which dampens pressure variations within a chamber housing the liquid to extend a period in which a membrane may be used and to reduce pressure variations downstream.

A further advantage of the present invention is to provide an apparatus, a system and a method for venting a gas from a liquid delivery system that is inexpensive to manufacture.

Another advantage of the present invention is to provide an apparatus, a system and a method for venting a gas from a liquid delivery system that efficiently vents the gas.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention relates to an apparatus, a system and a method for venting a gas from a liquid delivery system. To this end, the present invention may have a venting tube which may be positioned within a chamber. The venting tube may have an opening located at a bottom end of the venting tube. A liquiphobic, gas-permeable membrane may be adjacent to the opening. The chamber may hold a volume of liquid having an initial volume of gas trapped above the liquid. Additional gas may accumulate as a result of, for example, outgassing from the liquid, transportation of gas bubbles due to movement of the liquid through the chamber. The volume of liquid may have a top surface within the chamber. The membrane may be positioned on the venting tube at an angle wherein the membrane is not parallel to the top surface of the liquid. The liquid may contact the membrane due to additional liquid added to the chamber and gas venting from the chamber through the membrane. Gas within the chamber may escape through the membrane into the venting tube. However, because the membrane is not parallel to the top surface of the liquid contacting the membrane, the membrane may be less prone to clogging.

To this end, the liquid is introduced into the interior of the chamber to prime the liquid delivery system. The liquid may fill the chamber by displacing a portion of the gas initially present in the chamber. The displaced gas may be vented from the chamber by passing through the membrane and/or venting holes so that the liquid may partially fill the chamber to a point where the liquid covers the membrane and/or the venting holes to trap the remaining gas in the chamber. The liquid may pass into and out of the partially filled chamber such that any gas that may accompany the liquid into the chamber or any gas that forms within the liquid may enter the chamber and may rise to an upper portion of the chamber. The gas collects with a volume of the gas already trapped in the upper portion of the chamber.

As the gas accumulates within the chamber, the liquid level within the chamber is forced downward and may expose a small portion of the membrane to the gas. The excess gas volume may be vented from the chamber via the membrane and/or the vent holes, and venting may continue until the liquid level within the chamber again rises to the point at which the membrane is again covered by the liquid. An approximate liquid level equilibrium may be maintained wherein a relative constant gas volume is maintained in the upper portion of the chamber.

The gas trapped in the upper portion of chamber acts as a pressure damper. Pressure variations may be reduced wherein the peak pressure that may be applied to the membrane is reduced and the life of the membrane may be extended. Further, as the liquid continues to move through the chamber and as any accumulating gas continues to vent from the chamber via the membrane, the portion of the membrane that is venting the gas may become clogged with substances that may otherwise accompany the gas through the membrane. The gas may then no longer pass through a clogged portion of the membrane. As a result, gas volume may increase as additional gas enters the chamber so as to lower the liquid level thereby exposing an additional portion of the membrane surface to allow the venting activity to resume. As a result, a new liquid level equilibrium may be achieved such that the functional life of the membrane may be considerably increased.

Although the present invention may refer to a "membrane," it should be understood that a membrane refers to a hydrophobic, gas-permeable membrane. Alternatively, the membrane may be a liquiphobic membrane and should not be construed as limited to a hydrophobic membrane. A liquiphobic membrane may refer to a membrane that repels any liquid, including a membrane capable of repelling water.

In certain applications, i.e. medical applications where a sterile barrier is required, the gas-permeable membrane may have pores sized at 0.22 microns or less. Of course, for other applications, the pores may have a size of up to 0.35 microns or larger. It should, however, be appreciated that the present invention should not be construed as limited to the pore size. Still further, it should be understood that the present invention refers to "gas" hereinafter. The word "gas" also includes "air" and should be interpreted to include any gas and/or air.

Figure 1:
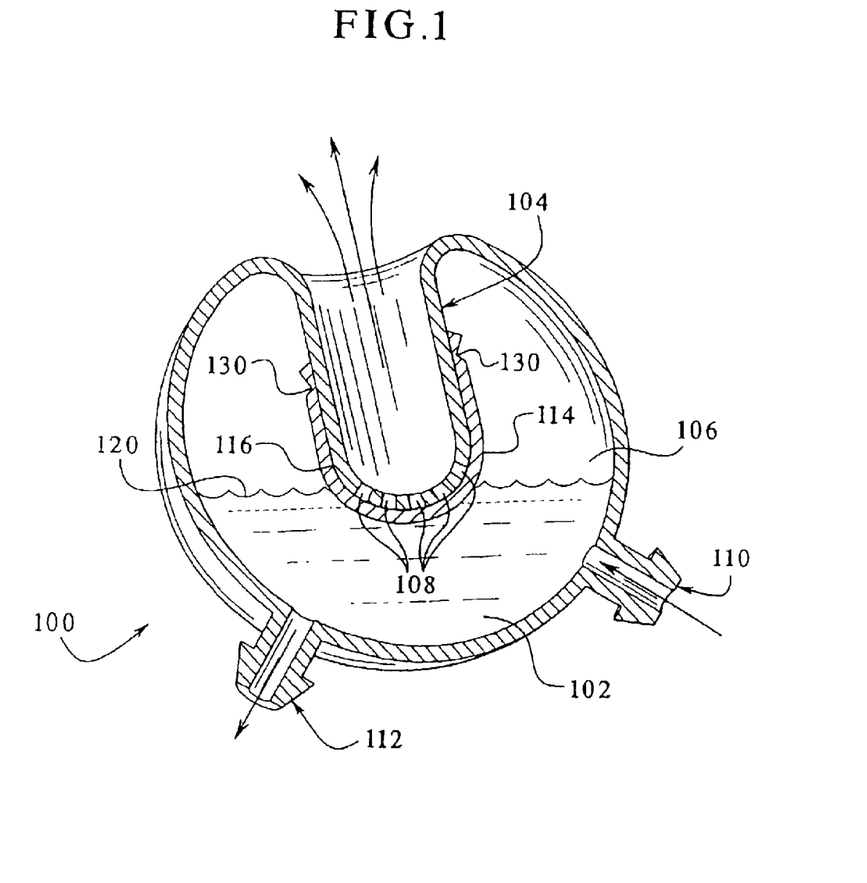
FIG. 1 illustrates a cross-sectional view of a chamber with an integrally formed venting tube in an embodiment of the present invention.

Referring now to the drawings, wherein like numerals refer to like parts, FIG. 1 illustrates a cross-sectional view of a chamber 100 which may contain a liquid 102 used in a liquid delivery system. The chamber 100 may be constructed from, for example, plastic or other rigid or semi-rigid polymer, metal, glass, or like material. The chamber 100 may have a depression 104 extending toward an interior 106 of the chamber 100. The depression 104 may have holes 108 which may enable gas (not shown) within the chamber 100 to escape from the chamber 100. A membrane 114 may be positioned on an inside surface 116 of the depression 104 and may cover the holes 108. The membrane 114 may be constructed from, for example, PTFE (polytetrafluoroethylene) or PVDF (polyvinylidene fluoride). The membrane 114 may be attached to the inside surface 116 by, for example, sealing the membrane 114 or an energy bond or a solvent bond. In an embodiment, the membrane 114 may be sealed to the inside surface 116 at points 130 above a surface 120 of the liquid 102. As previously set forth, the membrane 114 is gas-permeable and may be hydrophobic or liquiphobic.

The chamber 100 may have an input port 110 which may allow entry of the liquid 102 into the chamber 100. The chamber 100 may also have an exit port 112 which may allow the liquid 102 within the chamber 100 to exit the chamber 100. The liquid 102 may be delivered to the chamber 100, for example, in a continuous stream.

Addition of the liquid 102 to the chamber 100 and/or movement of the chamber 100 may cause an amount of gas within the chamber 100 to increase. Accumulation of the gas within the chamber 100 may cause an increase in pressure. The gas may then be forced through the membrane 114 and through the holes 108 to exit the chamber 100.

The gas may also pass through the membrane 114 when the liquid 102 contacts the membrane 114. Contact results from addition of the liquid 102 to the chamber 100 and/or by movement of the chamber 100. The membrane 114 may define a surface that is not parallel to the surface 120 of the liquid 102. As a result, the gas may pass through the membrane 114, and the membrane 114 may be less prone to clogging as previously described.

Figure 2:
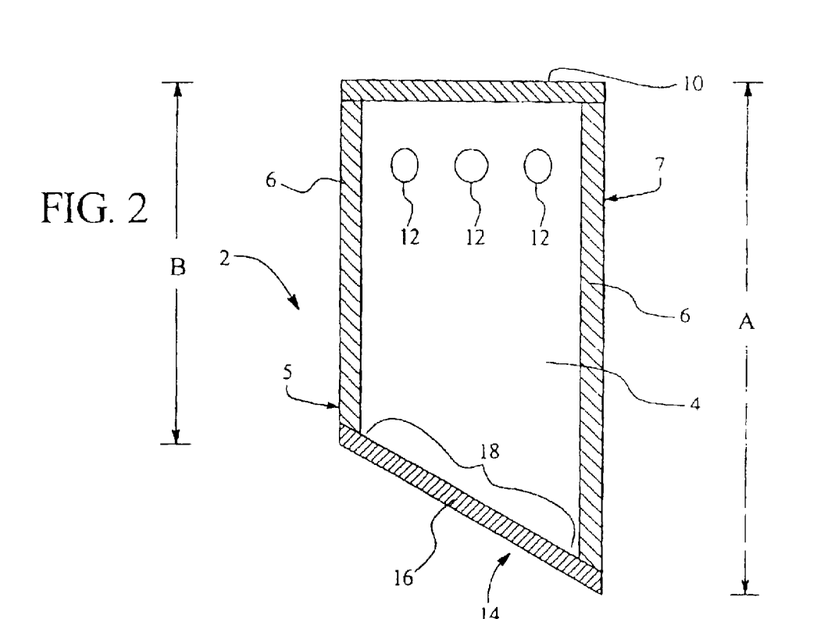
FIG. 2 illustrates a cross-sectional view of a venting tube in an embodiment of the present invention.
Figure 6:
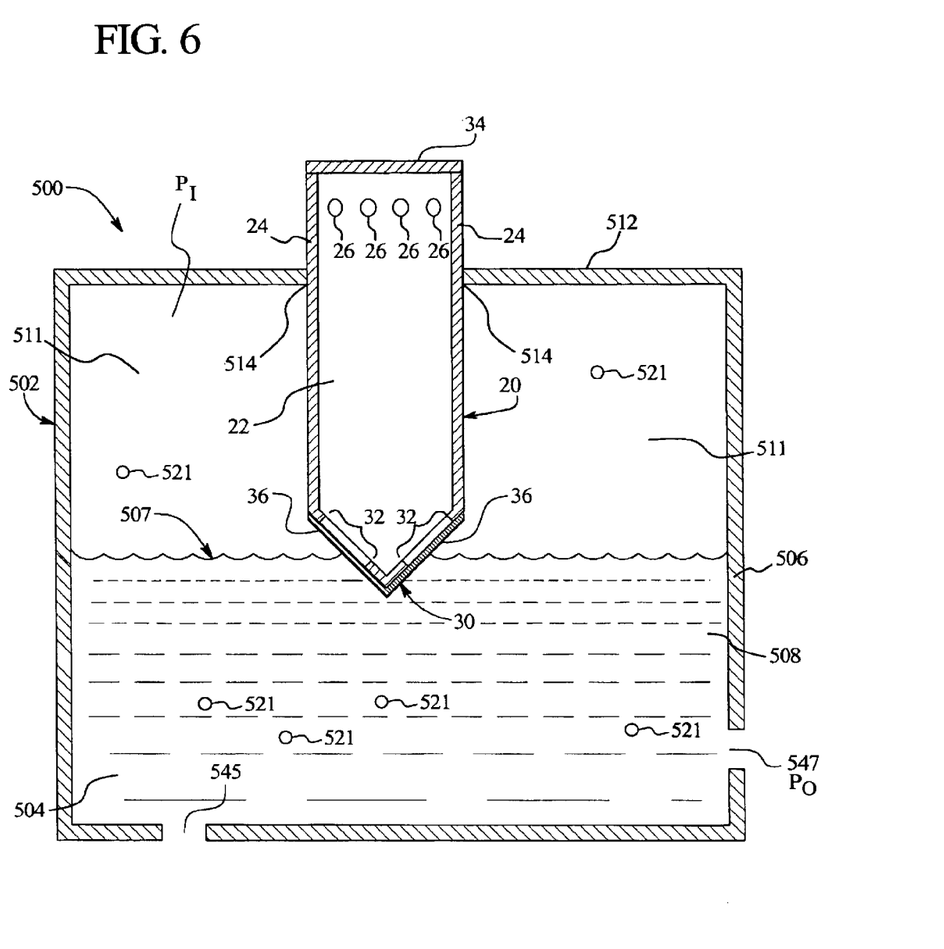
FIG. 6 illustrates a cross-sectional view of a venting tube positioned within a chamber in an embodiment of the present invention.

FIG. 2 illustrates a cross-sectional view of a venting tube 2 in an embodiment of the present invention. The venting tube 2 may be placed, for example, in communication with a chamber, such as a liquid-holding chamber 502 as illustrated in FIG. 6. The venting tube 2 may have an interior 4 defined by walls 6. In an embodiment, the venting tube 2 may be cylindrical. The walls 6 may be constructed from, for example, acrylic plastic. A top surface 10 may be provided having an area defined by a perimeter of the walls 6. The top surface 10 may define a plane. Venting holes 12 may be located in the walls 6 adjacent to the top surface 10.

The walls 6 may be sized wherein a first side 7 has a length A which may be greater than a length B of a second side 5. An opening 18 may be defined by the perimeter of the walls 6 at a bottom end 14 of the venting tube 2. The first side 7 and the second side 5 may define a plane of the opening 18 wherein the plane is not parallel to the plane defined by the top surface 10.

As shown in FIG. 2, a membrane 16 may cover the opening 18. The membrane 16 may be constructed from, for example, PTFE (polytetrafluoroethylene) or PVDF (polyvinylidene fluoride). The membrane 16 may define a surface that is not parallel to a top surface 507 of the liquid 504 when implemented in, for example, the embodiment illustrated in FIG. 6. The membrane 16 may prevent the liquid 504 from passing through the membrane 16 while allowing the gas 521 to enter into the interior 4 of the venting tube 2. The membrane 16 may be attached to the walls 6 of the venting tube 2 by, for example, sealing the membrane 16 or by an energy bond or a solvent bond. As previously set forth, the membrane 16 is gas-permeable and may be hydrophobic or liquiphobic.

The addition of liquid to the chamber 502 and/or movement of the chamber 502 may cause the gas 521 within the liquid 504 to form in a gas pocket 511 within the chamber 502. Accumulation of the gas 521 within the gas pocket 511 may cause an increase in pressure. The gas 521 may then be forced through the membrane 16 into the venting tube 2. The gas 521 may be vented through the venting holes 12.

The gas 521 may also pass through the membrane 16 when the liquid 504 contacts the membrane 16. Contact results from addition of liquid to the chamber 502 and/or by movement of the chamber 502. The membrane 16 may define a surface that is not parallel to the top surface 507 of the liquid 504. As a result, the gas 521 may pass through the membrane 16, and the membrane 16 may be less prone to clogging as previously described.

In an embodiment, the top surface 10 may be parallel to the plane of the opening 18. However, the venting tube 2 may be positioned within the chamber 502 wherein the membrane 16 may define a surface that is not parallel to the top surface 507 of the liquid 504. As a result, the gas 521 within the chamber 502 may be vented through the membrane 16, and the membrane 16 may be less prone to clogging as previously described.

Figure 3:
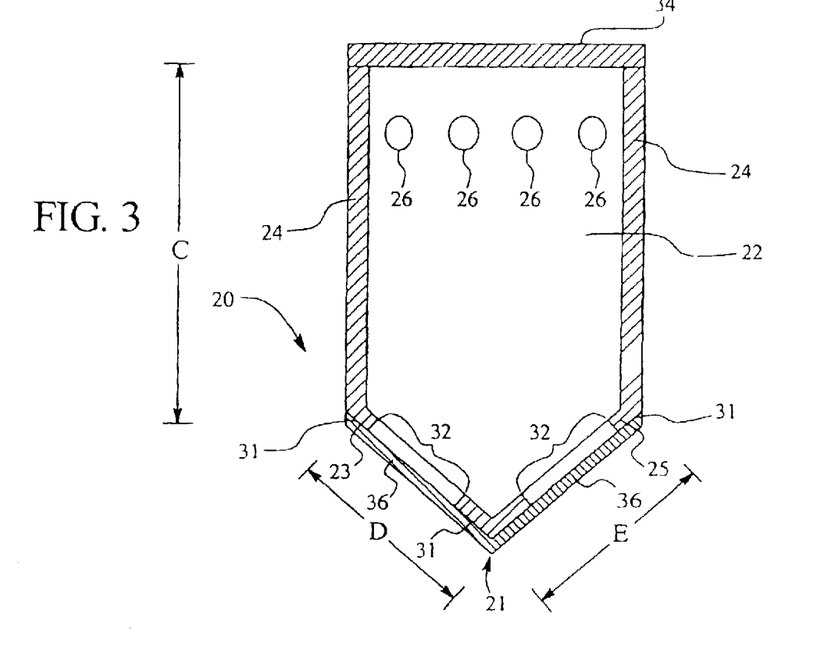
FIG. 3 illustrates a cross-sectional view of a venting tube in another embodiment of the present invention.

FIG. 3 illustrates another embodiment of a venting tube 20 having venting holes 26 and an interior 22 defined by walls 24. Preferably, the walls 24 defining the venting tube 20 are cylindrical in shape. The venting tube 20 may have a top surface 34 defined by a perimeter of the walls 24. The walls 24 may have a length C on a first side 23 and a second side 25. In addition, the walls 24 may form an apex 21 defined by a first length D on the first side 23 and a second length E on the second side 25. In an embodiment, the length D on the first side 23 and the length E on the second side 25 are equal in length. In another embodiment, the length D on the first side 23 and the length E on the second side 25 are not equal in length. Preferably, the first side 23 and the second side 25 form a right angle at the apex 21. More specifically, the first side 23 and the second side 25 may extend at a 45 degree angle with respect to a plane defined by the top surface 34. The walls 24 of the venting tube 20 may have holes 32 near the apex 21 as shown in FIG. 3.

A membrane 36 may be positioned on an exterior 31 of the venting tube 20 adjacent to the apex 21 of the venting tube 20. The membrane 36 may be sealed or otherwise attached to the venting tube 20 by, for example, an energy bond (e.g., heat or ultrasonic). The membrane 36 may also be attached to the venting tube 20 by, for example, a solvent bond. The membrane 36 may cover the holes 32. The membrane 36 may be a hydrophobic or liquiphobic membrane. The membrane 36 may be constructed from, for example, PTFE (polytetrafluoroethylene) or PVDF (polyvinylidene fluoride). In addition, the membrane 36 is gas-permeable and may prevent the liquid 504 from passing through the membrane 36 and may allow the gas 521 within the liquid 504 to enter into the interior 22 of the venting tube 20.

The venting tube 20 may be positioned within the chamber 502 illustrated in FIG. 6. The addition of liquid to the chamber 502 and/or movement of the chamber 502 may cause the gas 521 within the liquid 504 to transfer to the gas pocket 511 within the chamber 502. Accumulation of the gas 521 within the gas pocket 511 may cause an increase in pressure. The gas 521 may then be forced through the membrane 36 into the venting tube 20. The gas 521 may further be vented through the venting holes 26.

The gas 521 may also pass through the membrane 36 when the liquid 504 contacts the membrane 36. Contact may result from an addition of liquid to the chamber 502 and/or by movement of the chamber 502. Preferably, the membrane 36 may define a surface that is not parallel to a top surface 507 of the liquid 504. As a result, the gas 521 may pass through the membrane 36, and the membrane 36 may be less prone to clogging as previously described. As illustrated, the membrane 36 is integrally formed; however, the membrane 36 may be formed from a first membrane to cover one of the holes 32 and a second membrane to cover the other one of the holes 32 of the venting tube 20.

Figure 4:
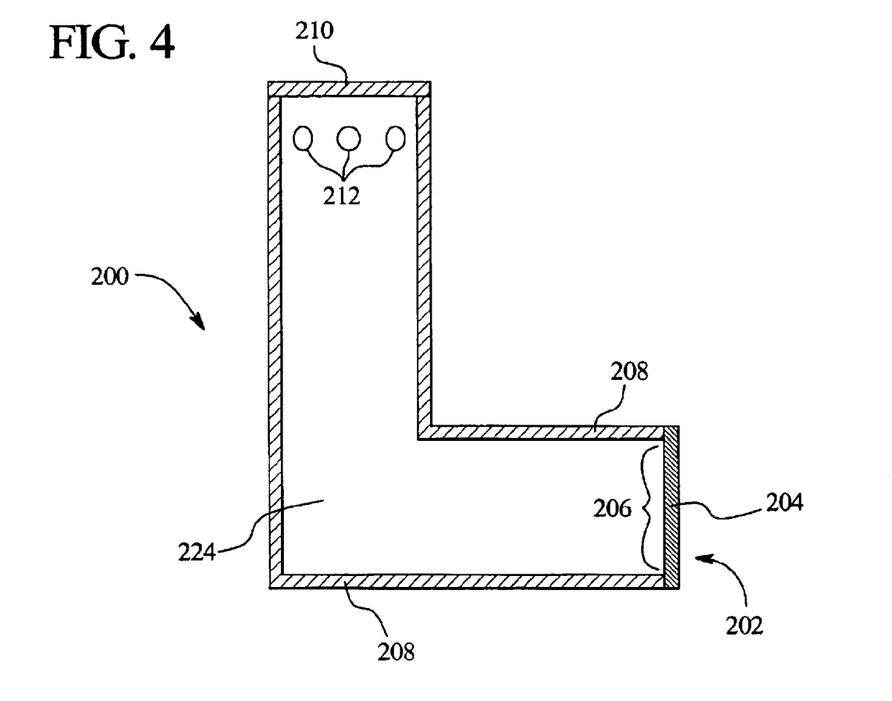
FIG. 4 illustrates a cross-sectional view of a venting tube in another embodiment of the present invention.

FIG. 4 illustrates another embodiment of a venting tube 200. The venting tube 200 may have venting holes 212 adjacent to a top surface 210. The venting tube 200 may also have walls 208 defining an L-shaped, cylindrical interior 224. A first end 202 of the venting tube 200 may have an opening 206 which may define a plane perpendicular to that of the top surface 210.

A membrane 204 may cover the opening 206. The membrane 204 may be constructed from, for example, PTFE (polytetrafluoroethylene) or PVDF (polyvinylidene fluoride). The membrane 204 may be sealed or otherwise attached to the venting tube 200 by, for example, energy or solvent welding. The membrane 204 may be a hydrophobic or liquiphobic membrane. Accordingly, the membrane 204 is gas-permeable and may prevent the liquid 504 from passing through the membrane 204 and may allow the gas 521 within the liquid to enter into the interior 224 of the venting tube 200.

The venting tube 200 may be positioned within the chamber 502 illustrated in FIG. 6. The addition of liquid to the chamber 502 and/or movement of the chamber 502 may cause the gas 521 within the liquid 504 to form within the gas pocket 511 within the chamber 502. Accumulation of the gas 521 within the gas pocket 511 may cause an increase in pressure. The gas 521 may then be forced through the membrane 204 into the venting tube 200. The gas 521 may further be vented through the venting holes 212.

The gas 521 may also pass through the membrane 204 when the liquid 504 contacts the membrane 204. Contact results from addition of liquid to the chamber 502 and/or movement of the chamber 502. Preferably, the membrane 204 may define a plane that is not parallel to a top surface 507 of the liquid 504. As a result, the gas 521 may pass from the liquid 504 into the venting tube 200, and the membrane 204 may be less prone to clogging as previously described.

Figure 5:
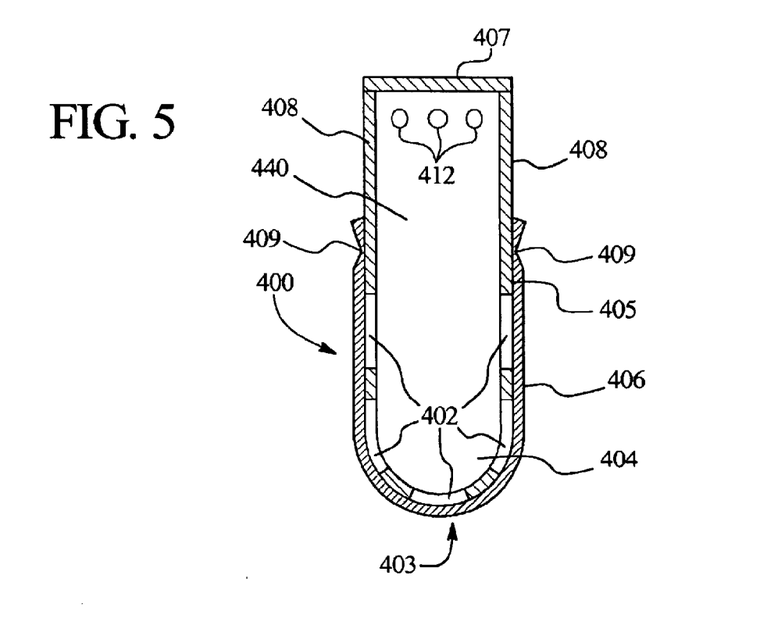
FIG. 5 illustrates a cross-sectional view of a venting tube in another embodiment of the present invention.

FIG. 5 illustrates another embodiment of a venting tube 400. The venting tube 400 may have walls 408 defining a cylindrical interior 440. The venting tube 400 may also have venting holes 412 within the walls 408 of the venting tube 400 adjacent to a top surface 407. The walls 408 may form a rounded end 403. Holes 402 may be provided in the walls 408 of the venting tube 400 as illustrated in FIG. 5.

A membrane 406 may be positioned on an exterior 405 of the venting tube 400. The membrane 406 may be constructed of PTFE (polytetrafluoroethylene) or PVDF (polyvinylidene fluoride). The membrane 406 may be a hydrophobic or liquiphobic membrane wherein the membrane 406 may prevent the liquid 504 from passing through the membrane 406 and may allow the gas 521 within the liquid to enter into the interior 404 of the venting tube 400.

The membrane 406 may be sealed or otherwise attached to the venting tube 400 at a point 409 located on the walls 408 between the opening 407 and the holes 402. As illustrated in FIG. 5, the membrane 406 may extend both above and below the holes 402. As a result, the gas 521 which may accumulate below the gas pocket 511 of the chamber 502 may pass through the membrane 406 for venting when the venting tube 400 is positioned within the chamber 502. The membrane 406 may be sealed or otherwise attached to the walls 408 of the venting tube 400 by, for example, energy or solvent welding.

The venting tube 400 may be positioned within the chamber 502 illustrated in FIG. 6. Moreover, the chamber 502 may contact the venting tube 400 at a point on the walls 408 between the venting holes 412 and the point 409. The liquid 504 within the chamber 502 may contact the membrane 406. Contact results from addition of liquid to the chamber 502 and/or movement of the chamber 502. As a result, the gas 521 within the liquid 504 may pass through the membrane 406 into the venting tube 400. The gas 521 may be removed through the venting holes 412. The membrane 406 may be positioned on the venting tube 400 wherein the membrane 406 may define a surface that is not parallel to the top surface 507 of the liquid 504. As a result, the membrane 406 may be less prone to clogging as previously described.

Addition of liquid and/or movement of the chamber 502 may also cause the gas 521 to form in the gas pocket 511 within the chamber 502. Accumulation of the gas 521 within the gas pocket 511 may cause an increase in pressure. The gas 521 may then be forced through the membrane 406 to the interior 440 of the venting tube 400. The gas 521 may be vented through the venting holes 412.

FIG. 6 illustrates a system 500 in which the gas 521 may be vented from a liquid 504. The chamber 502 may hold the liquid 504 which may be provided by, for example, a continuous stream from a remote source (not shown). The chamber 502 may be constructed from, for example, acrylic. In addition, the chamber 502 may have walls 506 defining an interior 508 of the chamber 502. The gas pocket 511 may be above a top surface 507 of the liquid 504 and may contain, or trap, the gas 521 within the chamber 502. A top surface 512 of the chamber 502 may have an opening 514. The chamber 502 may have an inlet 545 in the walls 506 for the addition of liquid. Further, the chamber 502 may have an outlet 547 positioned within the walls 506 for the removal of the liquid 504. The inlet 545 and the outlet 547 may be in any location of the walls 506. In a preferred embodiment, the inlet 545 and the outlet 547 are positioned in the walls 506 at a maximum distance apart from each other.

Any one of the venting tubes 2, 20, 200 and 400 described above may be positioned within the chamber 502. FIG. 6 illustrates the venting tube 20 positioned within the opening 514 of the chamber 502. The bottom end 30 may be positioned within the interior 508 of the chamber 502, and the top surface 34 may be positioned outside of the chamber 502.

The chamber 502 may also contain gas which is not present within the liquid 504. The gas may be due to changes in pressure, temperature, movement of the liquid 504 and/or gas delivered by the remote source, or the like. Addition of liquid to the chamber 502 or movement of the chamber 502 may cause an increase in pressure within the chamber 502. The increase in pressure may cause the gas within the chamber 502 to pass through the membrane 36. The gas may be vented through the venting holes 26.

If a large volume of the liquid 504 is present within the chamber 502 resulting from, for example, addition of liquid to the chamber 502, the top surface 507 of the liquid 504 within the chamber 502 may be at a height above the membrane 36. The addition of liquid to the chamber 502 may cause an increased amount of gas to collect within the gas pocket 511. Pressure created by the collection of gas may compress the volume of liquid 504, lowering the height of the top surface 507 and exposing an additional area of the membrane 36 for venting.

Figure 7:
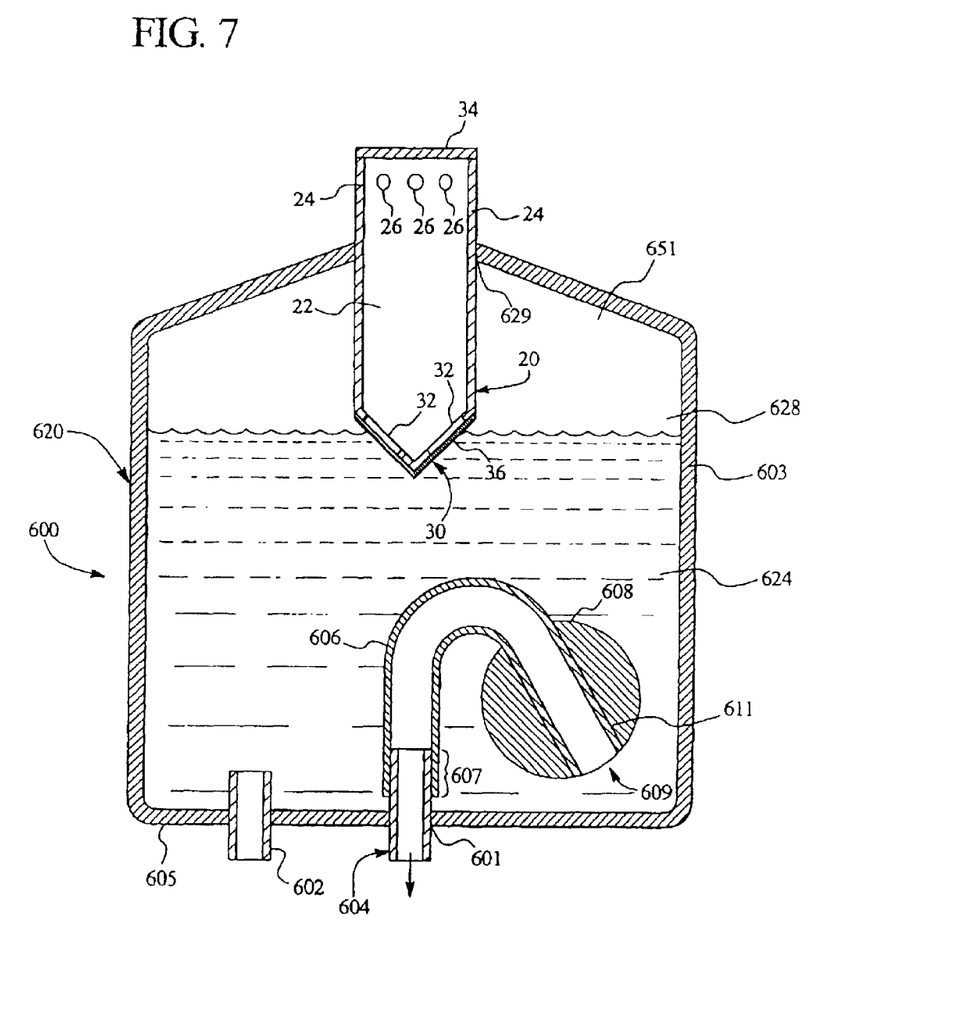
FIG. 7 illustrates a cross-sectional view of a system including a venting tube positioned within a chamber in another embodiment of the present invention.

FIG. 7 illustrates another embodiment of a system 600 for venting a gas in a gas pocket 651 from a liquid 624. The system 600 may have a chamber 620 having walls 603 defining an interior 628. A liquid input port 602 may be located at a base 605 of the chamber 620. A liquid exit port 604 may also be located at the base 605 of the chamber 620, preferably at or near a center 601 of the base 605. A portion of the liquid exit port 604 may be positioned within the interior 628 of the chamber 620. Attached to the liquid exit port 604 within the interior 628 of the chamber 620 may be a tube 606. The tube 606 may be attached to the liquid exit port 604 at an end portion 607. A weight 608 may be attached to the tube 606 on an exterior 611 of the tube 606 near an end 609 of the tube 606. The weight 608 may enable the tube 606 to remain submerged within the liquid 624. The chamber 620 may have an opening 629. FIG. 7 illustrates the venting tube 20 positioned within the opening 629; however, any one of the venting tubes 2, 20, 200, 400 may be positioned within the opening 629 of the chamber 620 for venting the gas in the gas pocket 651 from the liquid 624.

The apparatus, system and method for venting a gas from a liquid provide advantages for a liquid delivery system, such as, for example, a peritoneal dialysis liquid delivery system. The venting tube may have a membrane defining a plane that is not parallel to a top surface of a liquid within a chamber. The liquid contacting the membrane may then progress off of the membrane. Moreover, the membrane may be less prone to clogging during venting as previously described.

In addition, the membrane may vent gas from a liquid independent of the position maintained by the membrane within the chamber. The system may not require the surface of the liquid to be parallel to the membrane to vent gas from the liquid. As a result, the chamber may be re-positioned and gas may continue to pass through the membrane. Accordingly, the venting tube and the chamber may be implemented within, for example, a portable dialysis system which may accommodate a change in the position of the system. In an embodiment, the chamber may be tilted in a range from 0 to 360 degrees. Accordingly, the venting tube and the chamber may be implemented in, for example, a wearable kidney dialysis system in which a patient may move freely during dialysis. In this embodiment, the liquid within the chamber may move in an erratic and/or random manner. As a result, different areas of the surface of the membrane may be exposed to the liquid at different times. A time average of exposure of the membrane to the liquid is then reduced. As a result, the period in which the membrane may be used is extended.

In an embodiment, the venting tube and the chamber may function as a stand-alone unit which may be attached to a liquid bag. In another embodiment, the venting tube and the chamber may be implemented in a dialysis system which utilizes a liquid-pumping cassette.

The chamber may incorporate a gas trap within the gas pocket 511 which may act as a pressure damper. The gas trap may be beneficial in systems in which liquid pressure is non-constant, such as those utilizing a piston pump or the like. In general, changes in pressure may cause damage to the membrane. However, because the pressure within the system of the present invention may be dampened, the period in which the membrane may be used may be extended.

An example of a test using the venting device and the system of the present invention will be described with reference to the graph shown in FIG. 8. Downstream pressure ($P_O$) and intrachamber pressure ($P_I$) are shown in FIG. 6. In a first step, the chamber 500 may be primed, or filled with liquid 504. In a next step, additional liquid may be delivered into the chamber 502 through the inlet 545. The liquid may be delivered, for example, at a rate of 100 milliliters per minute. Air may be injected into the chamber 502. The air may have a flow rate of, for example, 15 milliliters per minute.

Figure 8:
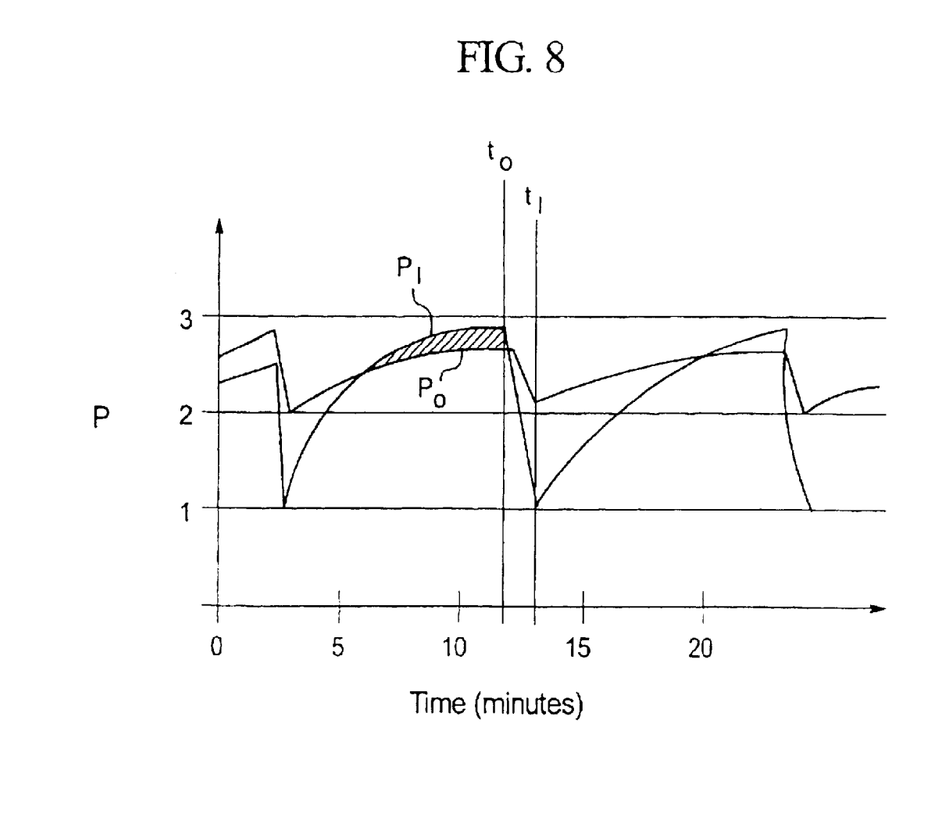
FIG. 8 illustrates a graph of pressure versus time within, and exterior to, a chamber in a liquid delivery system in an embodiment of the present invention.

As a result, at steady state, the outlet pressure ($P_O$) may increase as the air 521 and the liquid 504 may accumulate within the chamber 502, as shown in FIG. 8. In addition, the intrachamber pressure (PI) may increase as a level of the liquid 504 within the chamber 502 covers the membrane 36 and/or air continues to flow into the chamber 502. At a time $t_0$ indicated in FIG. 8, a difference in pressure between the intrachamber pressure and the outlet pressure ($P_I$–$P_O$) may cause the surface 507 of the liquid 504 to be lowered within the chamber 502. When the liquid level 504 reaches the venting membrane 36, and venting occurs, $P_I$ decreases as gas vents.

Further, at a time $t_1$ indicated in FIG. 8, the intrachamber pressure ($P_I$) may be equal to a sum of atmospheric pressure and a transmembrane pressure, or pressure of air venting through the membrane 36. As a result, the venting activity may stop. Then, the cycle repeats or reoccurs reaching a quasi-static equilibrium. After conducting the above test, it was observed that only a top portion of a membrane was clogged by contaminants during gas venting. Moreover, the non-parallel orientation of the membrane extended use of the membrane approximately 10–20 times longer than a membrane venting gas and having an orientation parallel to a liquid.

It should be understood that various changes and modifications to the presently preferred embodiments described herein will be apparent to those skilled in the art. Such changes and modifications may be made without departing from the spirit and scope of the present invention and without diminishing its attendant advantages. It is therefore intended that such changes and modifications be covered by the appended claims.

We claim:

1. A method for venting a gas from a liquid delivery system, the method comprising the steps of:
   holding a liquid having a surface within a chamber having an interior wherein a portion of the chamber extends into the interior wherein the portion which extends into the interior forms a non-parallel surface to the surface of the liquid and further has a hole and is configured so that the liquid surface contacts and disengages from the non-parallel surface as the liquid rises and falls within the chamber; and
   attaching a liquiphobic membrane to the portion of the chamber which extends towards the interior wherein the membrane is within the interior of the chamber and further wherein the liquiphobic membrane covers the hole and the life of the membrane is prolonged due to the non-parallel orientation the surface.

2. The method of claim 1 further comprising the step of: adding liquid to the interior of the chamber.

3. The method of claim 1 further comprising the step of: removing the gas from the chamber.

4. The method of claim 1 further comprising the step of: venting the gas through the hole in the portion of the chamber which extends towards the interior of the chamber.

5. The method of claim 1 wherein the liquiphobic membrane conforms to the shape of the non-parallel surface.

6. The method of claim 1 wherein the non-parallel surface is non-planar.

7. A method for venting a gas from a liquid delivery system, the method comprising the steps of:
   providing a tube having walls defining an interior wherein the tube has an opening;
   attaching a gas-permeable membrane to the tube wherein the membrane covers the opening; and
   placing the tube to extend within a chamber having walls defining an interior wherein the chamber holds the liquid having a top surface within the chamber and further wherein the membrane defines a surface that is not parallel to the top surface of the liquid, so that the liquid surface contacts and disengages from the non-parallel membrane as the liquid rises and falls within the chamber.

8. The method of claim 7 further comprising the step of: adding liquid in the interior of the chamber.

9. The method of claim 7 further comprising the step of: venting gas through the tube wherein the gas exits the tube exterior to the interior of the chamber.

10. The method of claim 7 further comprising the step of: the opening being a first opening and venting gas through second holes in the walls of the tube exterior to the interior of the tube.

11. The method of claim 7 further comprising the step of: providing a second opening in the tube wherein the second opening is covered by the membrane.

12. An apparatus for venting a gas from a liquid delivery system, the apparatus comprising:

a tube having an interior defined by walls having a length defined between a first end and a second end wherein the tube has a top surface at the first end wherein the top surface defines a plane;

an opening at the second end of the tube wherein the opening defines a plane wherein the plane of the opening is not parallel to the plane of the top surface; and a membrane covering immediately at the place defined by the opening of the tube wherein the membrane prevents the liquid from passing through the membrane and allows the gas to enter into the interior of the tube through the opening of the tube.

13. The apparatus of claim 12 further comprising:

a venting hole in the walls of the tube.

14. The apparatus of claim 12 wherein the plane defined by the opening is perpendicular to the plane defined by the top surface.

15. The apparatus of claim 12 wherein the walls of the tube form an apex at the second end.

16. The apparatus of claim 12 further comprising:

a second opening in the walls of the tube wherein the membrane covers the second opening.

17. The apparatus of claim 12 wherein the membrane is attached to the venting tube at a point on the wall between the top surface and the opening.

18. The apparatus of claim 12 wherein the walls of the tube at the second end are rounded.

19. A system for venting a gas from a liquid delivery system, the system comprising:

a first tube having walls defining an interior wherein the first tube has an end defining a first opening;

a chamber having walls defining an interior with an opening in one of the walls wherein the interior holds the liquid wherein the liquid has a top surface and further wherein the first tube extends into the interior of the chamber through the opening; and a membrane covering immediately at the end the first opening of the first tube wherein the membrane is gas-permeable and defines a surface that is not parallel to the top surface of the liquid.

20. The system of claim 19 further comprising:

a gas pocket within the interior of the chamber defined by a volume of the interior which does not contain the liquid.

21. The system of claim 19 further comprising:

a venting hole in the wall of the first tube wherein the venting hole is exterior to the walls of the chamber.

22. The system of claim 19 further comprising:

a liquid input port in one of the walls of the chamber.

23. The system of claim 19 further comprising:

a liquid exit port in one of the walls of the chamber.

24. The system of claim 19 further comprising:

a second opening in the walls of the first tube wherein the membrane covers the second opening.

25. The system of claim 19 wherein the walls of the first tube form an apex.

26. The system of claim 19 further comprising:

a second tube within the interior of the chamber wherein the second tube is attached to a weight.

27. An apparatus for venting a gas from a liquid delivery system, the apparatus comprising:

a chamber having a body defining an interior holding a liquid wherein the chamber traps gas within the interior;

a depression integrally formed with the body wherein the depression has an inside surface within the interior of the chamber wherein the liquid within the interior of the chamber has a surface defining a plane;

an input port on the chamber wherein the input port allows entry of the liquid into the chamber;

an exit port on the chamber wherein the liquid within the chamber exits the chamber through the exit port; and a liquiphobic membrane positioned on the inside surface of the depression wherein the liquiphobic membrane defines a surface Which is non-parallel to the plane defined by the surface of the liquid within the chamber.

28. The apparatus of claim 27 wherein the membrane is attached to the inside surface of the depression.

29. The apparatus of claim 27 further comprising:

a hole in the depression wherein the membrane covers the hole.

30. The apparatus of claim 27 wherein the input port is below the surface of the liquid.

31. The apparatus of claim 27 wherein the exit port is below the surface of the liquid.

* * * * *